United States Patent
Lakhotia et al.

(10) Patent No.: US 10,605,795 B2
(45) Date of Patent: Mar. 31, 2020

(54) METHOD FOR MEASURING GAS CONCENTRATIONS BASED ON SENSOR RESPONSE TIMES

(71) Applicant: H2Scan Corporation, Valencia, CA (US)

(72) Inventors: Vikas Lakhotia, Valencia, CA (US); An T. Nguyen Le, Stevenson Ranch, CA (US); G. Jordan Maclay, Richland Center, WI (US)

(73) Assignee: H2Scan Corporation, Valencia, CA (US)

( * ) Notice: Subject to any disclaimer, the term of this patent is extended or adjusted under 35 U.S.C. 154(b) by 0 days.

(21) Appl. No.: 14/624,400

(22) Filed: Feb. 17, 2015

(65) Prior Publication Data
US 2016/0238578 A1    Aug. 18, 2016

(51) Int. Cl.
*G01N 33/00* (2006.01)
*G01N 27/04* (2006.01)
*G01N 27/12* (2006.01)
*G01N 27/22* (2006.01)

(52) U.S. Cl.
CPC ......... *G01N 33/005* (2013.01); *G01N 27/046* (2013.01); *G01N 27/12* (2013.01); *G01N 27/228* (2013.01)

(58) Field of Classification Search
CPC .................................................. G01N 33/005
See application file for complete search history.

(56) References Cited

U.S. PATENT DOCUMENTS

| 3,759,083 A * | 9/1973 | Erickson | G01K 15/00 324/617 |
| 8,265,881 B1 | 9/2012 | Lakhotia et al. | |
| 2004/0261500 A1* | 12/2004 | Ng | B82Y 15/00 73/31.05 |

OTHER PUBLICATIONS

Hughes, R.C., et al, "Chemical Microsensors," Science, vol. 245, Oct. 4, 1991, pp. 74-80.
Hughes, R.C., et al., "Thin-Film Palladium and Silver Alloys and Layers for Metal-Insulator-Semiconductor Sensors," J. Appl. Phys., vol. 62, No. 3, Aug. 1, 1987, pp. 1074-1083.
Löfdahl, Mikael, et. al., Difference in Hydrogen Sensitivity Between Pt and Pd Field-Effect Devices, J. Appl. Phys., vol. 91, No. 7, Apr. 1, 2002, pp. 4275-4280.
Maclay, et al., "Use of Time-dependent Chemical Sensor Signals for Selective Identification," Sensors and Actuators, 20 (1989), 277-285, 9 pages.

* cited by examiner

*Primary Examiner* — Lisa M Caputo
*Assistant Examiner* — Alex T Devito
(74) *Attorney, Agent, or Firm* — Jeffrey G. Sheldon; Katherine B. Sales; Cislo & Thomas (57) ABSTRACT

A method for measuring hydrogen concentration in a gas includes exposing a PdNi alloy thin-film gas sensor to the gas, alternately controlling the temperature of the PdNi alloy thin-film gas sensor between a first temperature for a first period of time and a second temperature for a second period of time while the PdNi alloy thin-film sensor is exposed to the gas, continuously monitoring the resistance of the PdNi alloy thin-film gas sensor during the first and second periods of time, and calculating the hydrogen concentration as a function of a transient in the resistance of the PdNi alloy thin-film sensor measured at a time that the temperature transitions between the first temperature and the second temperature.

23 Claims, 8 Drawing Sheets

METHOD FOR MEASURING GAS CONCENTRATIONS BASED ON SENSOR RESPONSE TIMES

BACKGROUND

The present invention relates to techniques for employing gas sensors for measuring concentration information for one or more gasses in a fluid environment.

Numerous gas sensors are known in the art. Gas concentrations can be measured by observing the changes in electrical properties (for example, resistance or capacitance) of the sensors. Thus, resistive sensors, capacitive sensors, and semiconductor sensors such as transistor, or diode sensors are known in the art As a particular example, thin-film PdNi alloy resistors have been used to detect gasses such as hydrogen and measure its concentration. Hydrogen is soluble in PdNi and the resistivity of the thin-film PdNi alloy increases upon exposure to hydrogen and the amount of increase is proportional to the square root of hydrogen partial pressure. Some gas sensors, such as one that has a PdNi lattice, may have increased resistance or changed capacitance or a characteristic of the semiconductor as concentration of $H_2$ increases. For example, resistance may increase linearly in proportion to the levels of hydrogen in a PdNi lattice, which in turn is related to gaseous $H_2$ pressure as described by Sievert's law. This law holds that, at moderate pressures, concentration for hydrogen dissolved in solid metals is approximated by the following relationship:

$$c \approx s * p^{1/2}$$

where c is the concentration of dissolved hydrogen in equilibrium with gaseous hydrogen at pressure p, and s is Sievert's parameter.

For a given application, a gas sensing system can be designed to detect the pressure of a target gas, for example, $H_2$. In addition to the target gas pressure, however, there may be factors that can influence a gas sensor's measurements. For example, temperature of the gas sensor may influence measurements. To address this issue, a heater may be used to maintain the gas sensor within a desired temperature range. In addition to temperature, other factors may influence gas sensor measurements, such as a bias voltage applied to the gas sensor or the overall pressure of the fluid environment. These measurements are also prone to errors due to baseline drift associated with aging and the presence of unwanted gases, and shifts in the sensor calibration. One solution to this problem is to employ a system that performs calibrations and performs gas measurements at two different temperatures.

Non-target gasses, such as $O_2$, may also influence a gas sensor's measurements. The presence of non-target gasses may influence or interfere with target gas measurements in at least two ways. First, because the sensor is responding to both a target and a non-target gas, the sensor reading may be too high or too low. In this respect, the influence of the non-target gas may be thought of as an offset to the target gas reading. Second, the presence of a non-target gas can alter the way a sensor measures a target gas. For example, non-target gasses can occupy receptor sites inside or on the surface of the lattice. This leaves less available receptor sites, thereby making the sensor less sensitive to the target-gas. As another example, in a PdNi gas sensor, the presence of oxygen in the lattice may affect the resistive or capacitive characteristics of the sensor. Thus, an oxygen-permeated lattice may respond to the presence of hydrogen in a different way than if the lattice was not permeated with oxygen. When oxygen permeates the lattice adsorption of hydrogen results in the formation of molecules such as $H_2O$, OH, etc. These molecules may, by themselves, influence the resistive or capacitive characteristics of the gas sensor.

One attempted solution for reducing the influence of non-target gasses may be to use a blocking coating on a gas sensor to filter such non-target gasses. However, such a filter may reduce a gas sensor's sensitivity or response time. Another attempted solution may be to use multiple gas sensors to specifically detect non-target gasses to determine and account for concentration information for non-target gasses. However, such a solution may be expensive and/or introduce additional system complexity. Yet another attempted solution is to simply limit gas-sensing applications to ones that do not include interfering gasses. A solution to the drift problem is to repeatedly recalibrate a drifting sensor manually.

Therefore, there is a need for a new method for detecting hydrogen and measuring its concentration, which does not suffer from these disadvantages.

SUMMARY

The present invention provides a solution for measuring the concentration of hydrogen, without the adverse effect of sensor drift. According to the present invention, the response times of the change in electrical parameters exhibited by gas sensors due to changes in temperature and hydrogen concentration are used to measure the absolute concentrations and variations in concentration.

According to one embodiment, the response times of the resistance change of resistors formed from certain metals and their alloys due to changes in resistor temperature and hydrogen concentration are used to measure the absolute concentrations and variations in concentration. Non-exhaustive examples of some materials that could be used for a hydrogen gas sensor include palladium, platinum, iridium, nickel, tungsten oxide, or alloys of palladium, platinum, iridium or nickel.

BRIEF DESCRIPTION OF THE DRAWING FIGURES

These and other features, aspects and advantages of the present invention will become better understood with regard to the following description, appended claims, and accompanying drawings where:

DESCRIPTION

According to the present invention, the response times of the change in electrical parameters exhibited by gas sensors due to changes in temperature and hydrogen concentration are used to measure the absolute concentrations and variations in concentration.

According to an embodiment of the present invention, the response times of the resistance change of resistors formed from certain metals and their alloys due to changes in resistor temperature and hydrogen concentration are used to measure the absolute concentrations and variations in concentration. Non-exhaustive examples of some materials that could be used for a hydrogen gas sensor include palladium, platinum, iridium, nickel, tungsten oxide, or alloys of palladium, platinum, iridium or nickel.

According to one embodiment of the present invention, the response times of the resistance change of gas sensor resistors due to changes in resistor temperature and hydrogen concentration are used to measure the absolute concentrations and variations in concentration.

According to another embodiment of the present invention, characteristics of spiking transients of the resistance change of gas sensor resistors to changes in resistor temperature and hydrogen concentration are used to measure the absolute concentrations and variations in concentration.

According to another embodiment of the present invention, other indicia, including but not limited to maximum/minimum values, rate of change of the first derivative, slope and slope ratio, and other characteristics of the steady-state or transient resistance change of gas sensor resistors due to changes in resistor temperature and hydrogen concentration are used to measure the absolute concentrations and variations in concentration.

Figure 1:
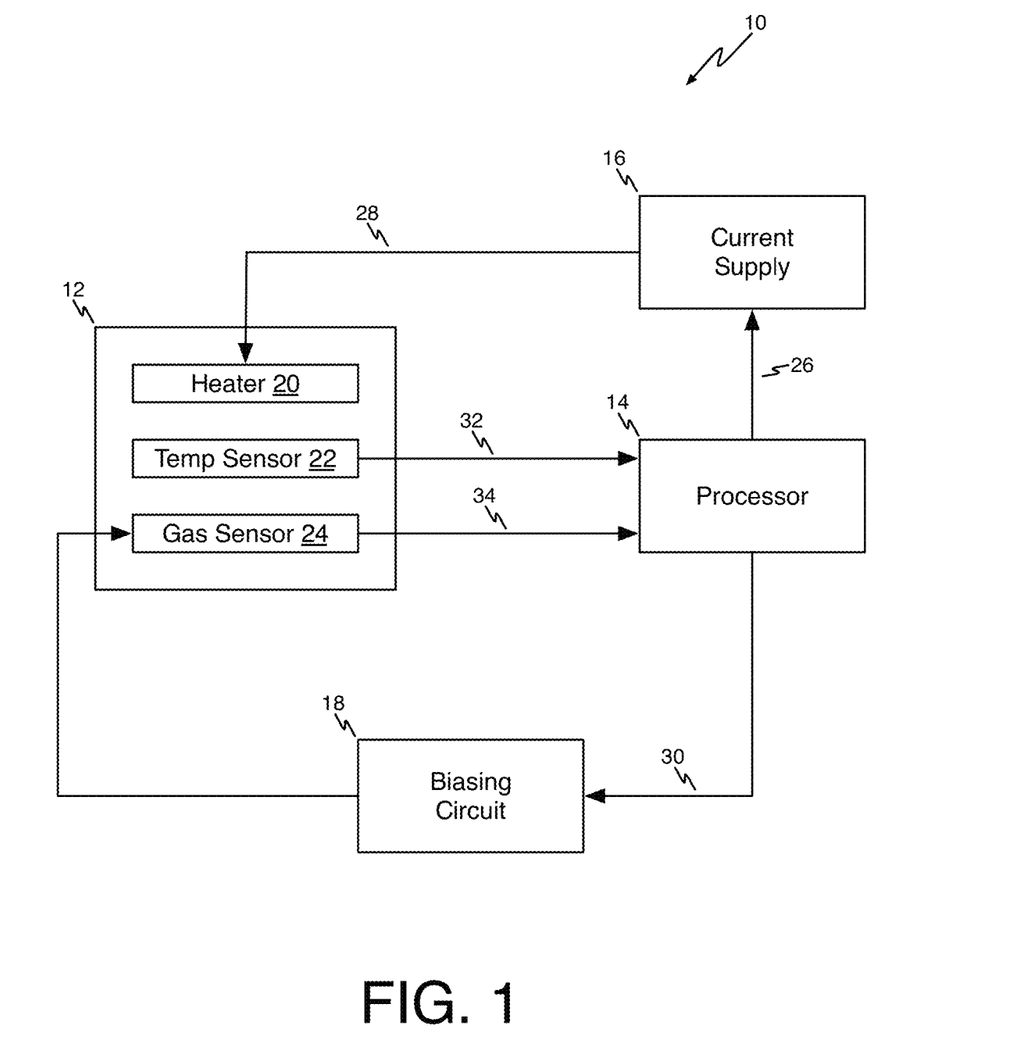
FIG. 1 is a diagram showing an illustrative gas sensing system that can be employed in the present invention.

FIG. 1 shows a gas sensing system 10, according to an embodiment of the present application. The system 10 may include a sensing unit 12, a processor 14, a current supply 16, and a biasing circuit 18. The sensing unit 12 may include a heater 20, a temperature sensor 22, and a gas sensor 24.

Gas sensor 24 may, for example, be a sensor that changes electrical resistance in response to exposure to different concentrations of a target gas. The response times of the resistance change of resistors formed from certain metals and their alloys due to changes in resistor temperature and hydrogen concentration are used to measure the absolute concentrations and variations in concentration. Non-exhaustive examples of some materials that can be used for a hydrogen gas sensor include palladium, platinum, iridium, nickel, tungsten oxide, or alloys of palladium, platinum, iridium or nickel.

The processor 14 may communicate a signal on line 26 to the current supply 16. In response to the signal on line 26, the current supply 16 may deliver an appropriate current to the heater 20 through line 28. The processor 14 may also communicate a signal on line 30 to the biasing circuit 18. In response to the signal on line 30, the biasing circuit 18 may apply an appropriate bias voltage to the gas sensor 24.

The processor 14 may include sub-processing portions, such as a digital signal processor. The processor 14 may be capable of executing a set of instructions from a computer-readable medium that effects gas measurement methods, such as the ones disclosed herein. The processor 14 may receive input data from a user interface (not shown), and may provide displayable data to a display (not shown).

The processor 14 receives temperature information from temperature sensor 22 on line 32 and receives gas concentration information from the gas sensor 24 on line 34.

The heater 20 may be capable of controlling the temperature of a sensing environment including the gas sensor 24. The heater 20 may be a resistive heater. The heater 20 may be employed by the processor 14 to control the temperature of a substrate in the gas sensor 24 by controlling the current flowing through the heater in a closed-loop with the temperature sensor 22 as is known in the art.

The gas sensor 24 may sense the presence of one or more gasses in a fluid environment and communicate concentration information corresponding to concentration(s) of the one or more gasses to the processor 14. It should be understood that the term "concentration information" may refer to any information that may be used to infer or estimate concentration(s) of one or more gasses in a target environment. For example, in accordance with other embodiments of the present invention, "concentration information" may include information about or derived from electrical characteristics of a sensor such as current or voltage or resistance or capacitance or some other semiconductor characteristic information.

As non-limiting examples, semiconductor gas sensors can be configured using alloys of PdAg as exemplified in Hughes, R. C., et. al., Thin-film palladium and silver alloys and layers for metal-insulator-semiconductor sensors, J. Appl. Phys., Vol. 62, No. 3, August 1987; Lofdahl, M., et. al., Difference in hydrogen sensitivity between Pt and Pd field-effect devices, J. Appl. Phys., Vol. 91, No. 7, April 2002. Capacitive gas sensors are also known, as exemplified by Hughes, R. C. et. al., Chemical Microsensors, Science, Vol. 254, pp. 74-80 October 1991. These references are expressly incorporated by reference herein.

A fluid environment may include a mixed atmosphere that has one or more gasses with variable concentrations. These gasses may include, for example, $H_2$ and $O_2$. The mixed atmosphere may also include other constituent gasses, such as $H_2O$, CO, $H_2S$, $Cl_2$, and $N_2$. A fluid environment may also include a liquid with dissolved gasses, such as the ones listed above.

Figure 2A:
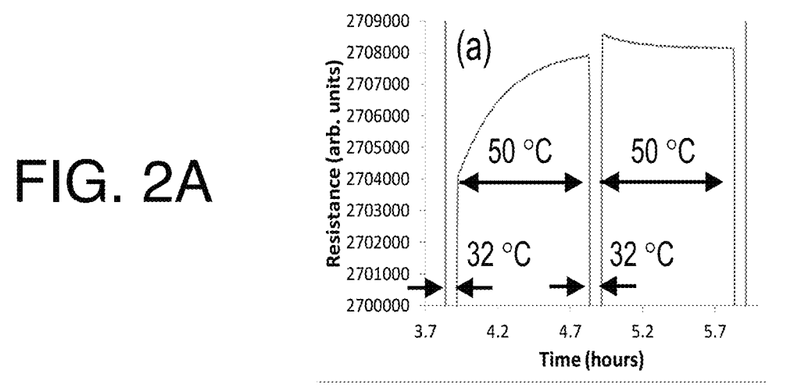
FIG. 2A is a diagram that shows the response times of the resistance change of PdNi resistors due to changes in resistor temperature at a hydrogen concentration of 1000 ppm over two temperature cycles alternating between 32° C. and 50° C. applied to the PdNi sensing element.
Figure 2B:
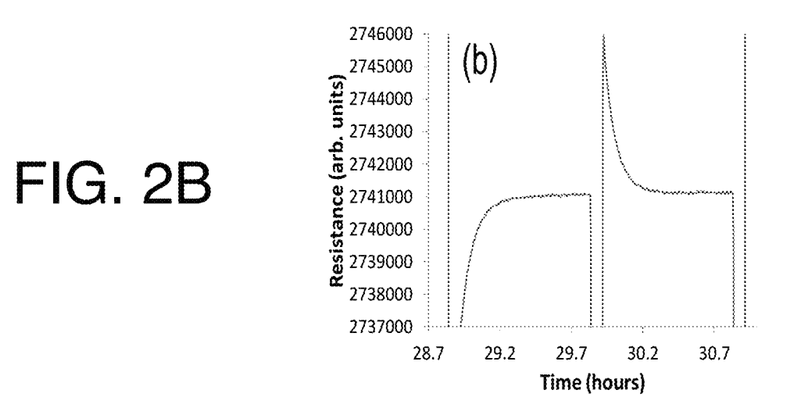
FIG. 2B shows the response times of the resistance change of PdNi resistors due to changes in resistor temperature at a hydrogen concentration of $10^4$ ppm over two temperature cycles alternating between 32° C. and 50° C. applied to the PdNi sensing element.
Figure 2C:
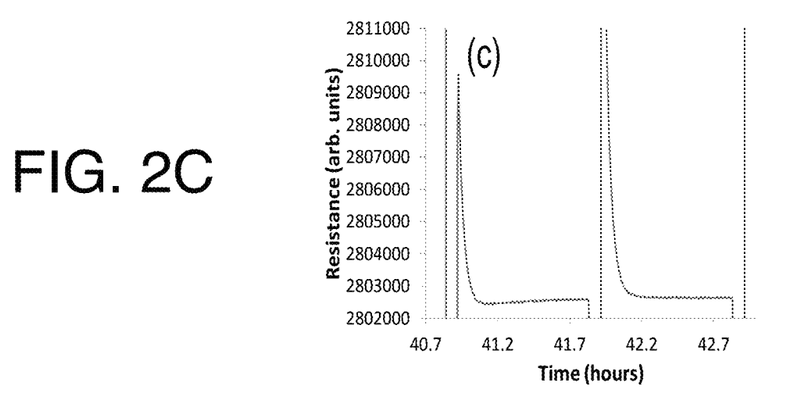
FIG. 2C shows the response times of the resistance change of PdNi resistors due to changes in resistor temperature at a hydrogen concentration of $5 \times 10^4$ ppm over two temperature cycles alternating between 32° C. and 50° C. applied to the PdNi sensing element.

Referring now to FIGS. 2A through 2C, diagrams show the response times of the resistance change of PdNi resistors due to changes in resistor temperature at a hydrogen concentration of $1 \times 10^3$, $1 \times 10^4$, and $5 \times 10^4$ ppm respectively over two temperature cycles applied to the PdNi sensing element. The hydrogen in the ambient enters the lattice of the PdNi sensor, and causes the resistance of the sensor to increase due to scattering of the conduction electrons by the hydrogen. The solubility of hydrogen in the PdNi sensing element decreases as the temperature increases, which means the sensitivity to hydrogen decreases with temperature. By making use of the temperature dependence of the hydrogen signal, and the different temperature dependence of other gases in the ambient on the signal, such as oxygen, it is possible to determine the hydrogen concentration. According to one exemplary and non-limiting embodiment, the temperatures are alternated between 32° C. and 50° C., the temperature being held at 32° C. for a period of 10 minutes, and being changed to and held at and 50° C. for a period of 60 minutes. With the apparatus used for these particular experiments, the temperature of the sensor could be changed within about 30 seconds, hence the temperature change from 32° C. to 50° C. or 50° C. to 32° C. appears as a vertical line with the scale used in FIGS. 2A through 2C. The times at which the temperatures are held at each of the two temperatures may vary according to pre-defined limits, or be dynamically adjusted for maximum sensitivity. Persons of ordinary skill in the art will appreciate that two other temperatures may be selected for performing the method of the present invention. Indeed a variety of temperature profiles that change with time are readily possible, and sensor measurements may be taken before or after the signal has reached a steady state.

FIG. 2A shows the response time at a hydrogen concentration of 1000 ppm, over two temperature cycles alternating between 32° C. and 50° C. applied to the PdNi sensing element. The temperature prior to the first 32° C. cycle was 70° C. The scale is such that the resistance at 70° C. is off scale upwards. Also the resistance at 32° C. is off scale downwards.

FIG. 2B shows the response times of the resistance change of PdNi resistors to changes in resistor temperature at a hydrogen concentration of $10^4$ ppm over two temperature cycles alternating between 32° C. and 50° C. applied to the PdNi sensing element. The temperature prior to the first 32° C. cycle was 70° C. The scale is such that the resistance at 70° C. is off scales upwards. Also the resistance at 32° C. is off scale downwards.

FIG. 2C shows the response times of the resistance change of PdNi resistors to changes in resistor temperature at a hydrogen concentration of $5 \times 10^4$ ppm over two temperature cycles alternating between 32° C. and 50° C. applied to the PdNi sensing element. The temperature prior to the first 32° C. cycle was 70° C. The scale is such that the resistance at 70° C. is off scale upwards. Also the resistance at 32° C. is off scale downwards.

In FIGS. 2B and 2C, two temperature cycles similar to the temperature cycle of FIG. 2A (32° C. to 50° C.) are applied to the PdNi sensor element. The resistance plot is slightly different for the first (leftmost) cycle and the second cycle (on the right). Before the first cycle begins, the temperature is 70° C., which drives out most of the hydrogen from the PdNi lattice. Consequently the resistance starts from a lower value than in the second cycle, which begins with the sensor coming from 50° C. For repeated 32° C.-50° C. cycles, the sensor waveform will stabilize, and look like the second (rightmost) cycle plotted.

The transients in the resistance signal are a function of hydrogen concentration. Namely, the response time decreases with hydrogen concentration and the overshoot increase. The solubility of $H_2$ in PdNi is much higher at lower temperatures.

Figure 3:
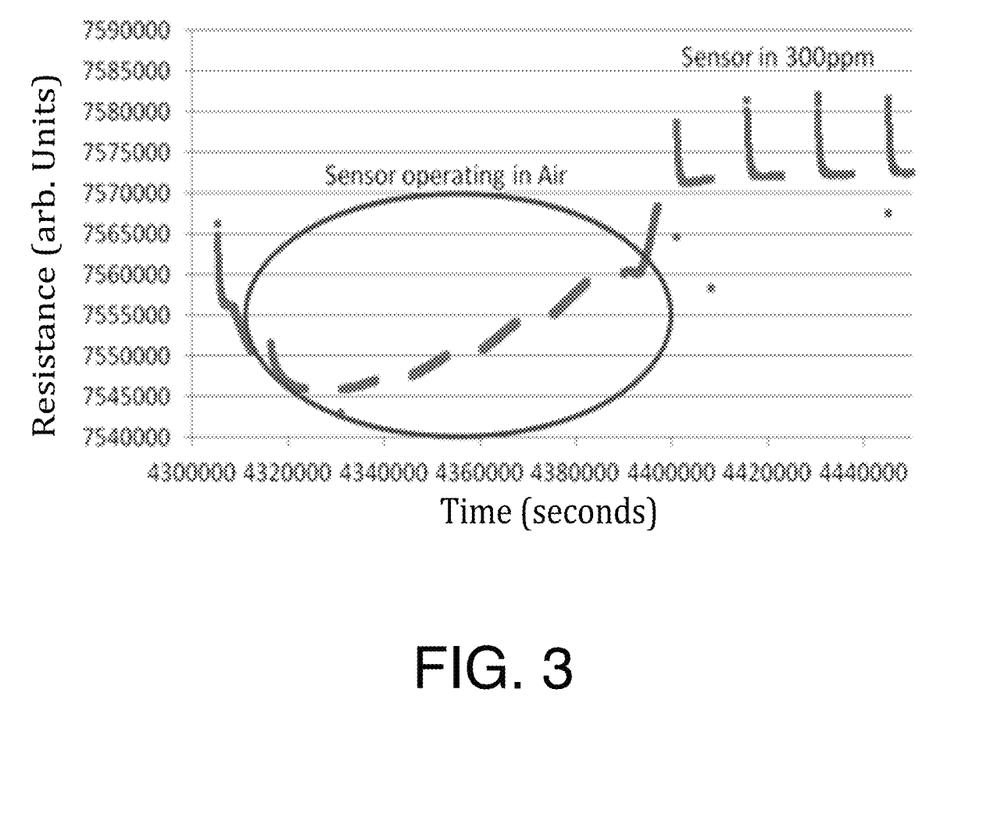
FIG. 3 shows the effect of repeated temperature cycles, as the ambient transitions from air to air including 300 ppm of hydrogen.

The increase in resistance as a function of $H_2$ concentration can also be seen from an examination of FIG. 3, in which the resistance measurements from multiple temperature cycles are shown. The plot shows both lower resistance values and absence of spiking transients following low-to-high temperature changes when the sensor is operating in ambient air. FIG. 3 also shows an increase in resistance values and spiking transients following low-to-high temperature changes as $H_2$ is introduced to the sensor environment and stabilizes at a concentration of 300 ppm. While the sensor resistance is drifting upward in air, there are no transients observed in the absence of hydrogen. When the ambient atmosphere is transitioned to 300 ppm of hydrogen in air, the transients can clearly be observed.

From an extrapolation between the curves of FIGS. 2B and 2C, it may be seen that there will be a threshold value of $H_2$ concentration at which the spiking transient starts to form. This characteristic of the resistance curve can be used as a threshold detector for hydrogen concentration by, for example, detecting a sign change in the first derivative of the resistance curve immediately following a low-to-high temperature transition. The slope of the spike can also be calibrated to $H_2$ concentrations.

In addition, the techniques of the present invention can be used to detect $H_2$ concentrations in the absence of spiking transient behavior of the resistance curves. For example, it can be observed from FIGS. 2A and 2B that the magnitude of the slope of the first or second cycle resistance curves increases more rapidly as a function of $H_2$ concentration. Examination of the rate of change of the slopes of the resistance curves in the first and second cycles of FIGS. 2A and 2B can be calibrated to $H_2$ concentrations.

Figure 4:
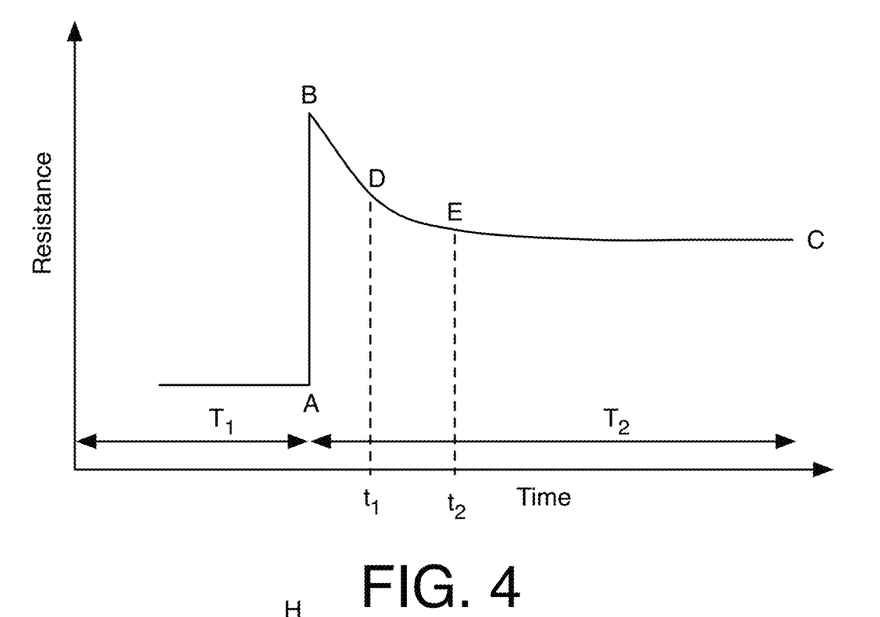
FIG. 4 is a graph showing a technique for performing dynamic H2 concentration measurement according to an aspect of the present invention.

Referring now to FIG. 4, a graph of resistance as a function of time and change in ambient temperature illustrates calculating hydrogen concentration according to another aspect of the present invention. During a first period of time the temperature in the measuring apparatus is set at temperature $T_1$. At point A on the curve the temperature in the measuring apparatus is raised to temperature $T_2$ and the resistance increases to the value at point B on the curve and then decreases to a steady state value represented by C on the curve. In FIG. 4, the temperature change from T1 to T2 is very rapid. In other embodiments, the temperature may change more slowly.

The resistance at time $t_1$ is represented by D on the curve and the resistance at time $t_2$ is represented by E on the curve. The change in resistance (delta) between points D and E correlates to the $H_2$ concentration. Higher $H_2$ concentration results in a larger delta and conversely a lower $H_2$ concentration results in a smaller delta between the resistances values between points D and E on the curve.

The resistance behavior can be represented by:

$$R_D - R_E = KH_2$$

or $$R_D - R_E = f(H_2)$$

where K is a constant of proportionality which decreases with increasing temperature.

If the sensor drifts over time, the DE delta ($R_D - R_E$) is no longer equal to its value obtained from calibration, and this drift can result in an erroneous $H_2$ concentration output. To avoid this, drift in sensor behavior must be dynamically calculated and corrected.

Several techniques can be used for drift elimination. According to a first illustrative and non-limiting technique, the resistances at points D and E are measured and the dynamic $H_2$ level is estimated. The $H_2$ concentration can also be calculated using a steady state method such as that disclosed in U.S. Pat. No. 8,265,881 (the entirety of which is incorporated herein by reference), and compared with the estimated dynamic $H_2$ level to verify that the two readings match. If the $H_2$ values as calculated from the dynamic method do not match the $H_2$ level from the steady-state method, it may be assumed that the sensor has drifted or the $H_2$ concentration has changed during the measurement and the $H_2$ values from the steady state method can be used to correct the dynamic H2 values. A new proportionality constant can be calculated from the new DE delta, and the dynamic calibration curve can be adjusted with this new constant. This proportionality constant can be dynamically calculated from every temperature change and the calibration curve can be constantly corrected to eliminate any drift effects.

Figure 5:
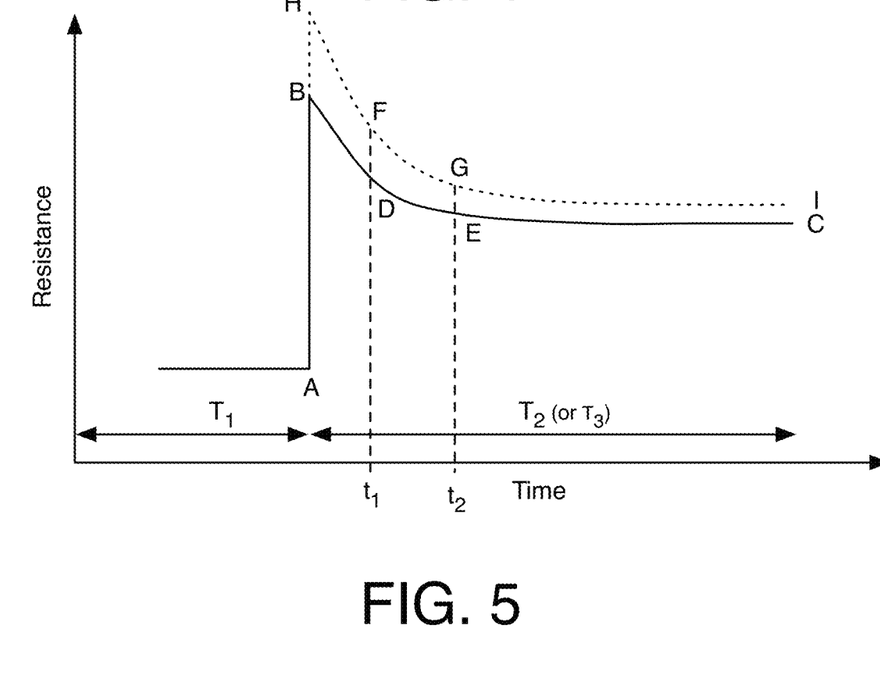
FIG. 5 is a graph showing a technique for performing dynamic H2 concentration measurement according to another aspect of the present invention.

According to a second illustrative and non-limiting technique illustrated in FIG. 5, temperature response from two different temperature spikes can be analyzed. As previously noted, a higher temperature spike results in a greater delta. The solid-line curve is from a first temperature transition from a temperature $T_1$ to a higher temperature $T_2$. The dashed-line curve is from a second temperature transition from a temperature $T_1$ to a higher temperature $T_3$, where $T_3 > T_2$.

At point A on the solid-line curve the temperature in the measuring apparatus is raised to temperature $T_2$ and the resistance increases to the value at point B on the curve and then decreases to a steady state value represented by C on the curve. The solid-line and dashed line curves are equal until point A, where on the dashed-line curve the temperature in the measuring apparatus is raised to temperature $T_3$ and the resistance increases to the value at point H on the curve and then decreases to a steady state value represented by I on the curve. The delta DE on the solid-line curve represents the resistance change for the lower temperature increase and the delta FG on the dashed-line curve represents the resistance change for the higher temperature increase.

The ratio of the deltas between DE and FG is dependent only on the $H_2$ level and the temperatures $T_1$, $T_2$, and $T_3$ and it can used to calculate the actual $H_2$ level:

$$\frac{R_D - R_E}{R_F - R_G} = f(H_2)$$

This ratio is insensitive to changes in the calibration of the sensor due, for example, to environmental contaminants depositing on the sensor surface, or changes in the film structure.

In another non-limiting embodiment, the slopes of the segments BD (or DE) and HF (or FG) can be separately calibrated to hydrogen concentration. If the corresponding $H_2$ concentrations obtained are equal, then the value is acceptable. If the values disagree, then recalibration, as has been discussed, will be necessary to obtain a reliable value of the $H_2$ concentration.

Any shifts in the individual delta e.g. the DE delta can be corrected for the sensor drift by calculating a new proportionality constant using the techniques disclosed herein.

Other calibration techniques may be applied to the data of the present invention. For example, calibration may be performed at a number of data points and a polynomial is then fit to the points to obtain the transfer curve.

Resistance measurements for calibration may be done at any time during the temperature cycle.

Figure 6:
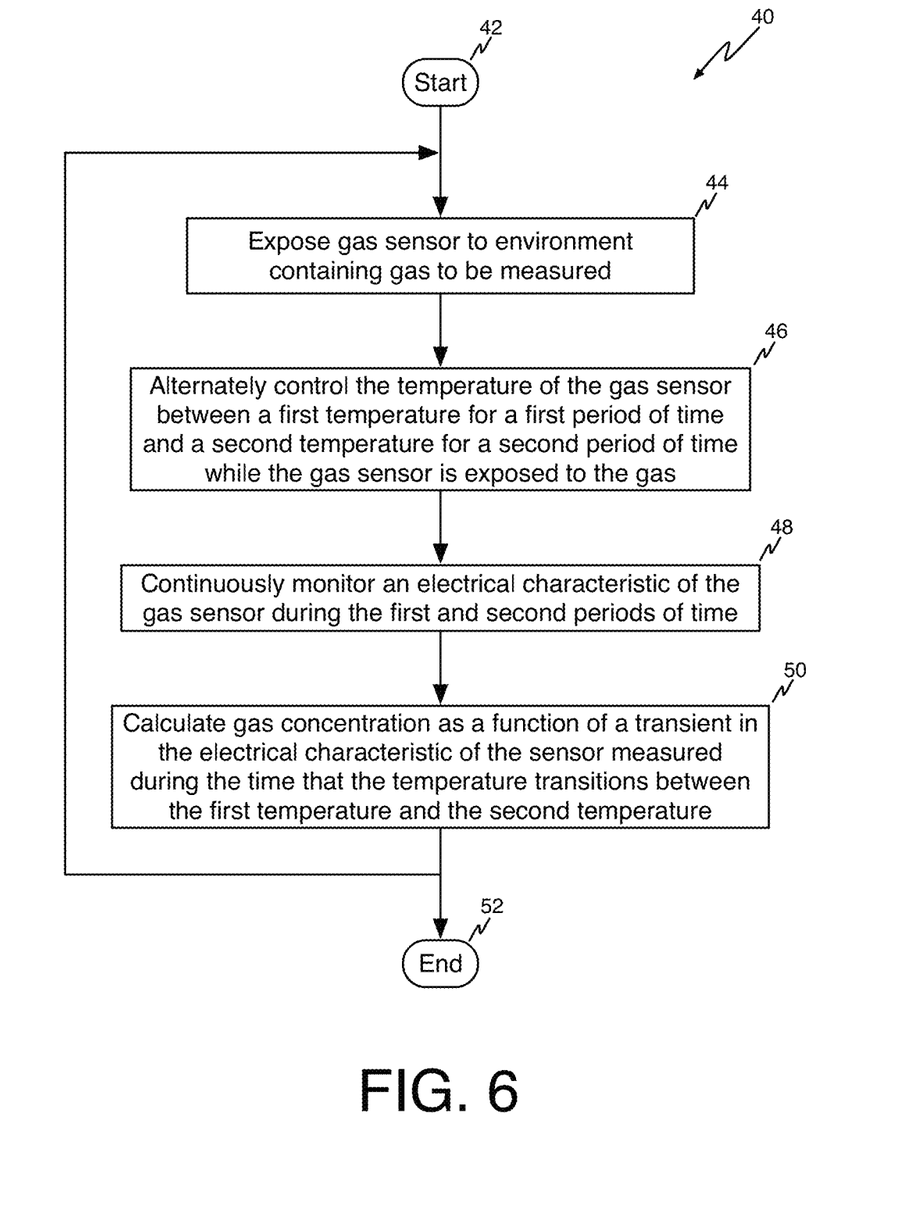
FIG. 6 is a flow diagram that shows an illustrative method according to one aspect of the present invention.

Referring now to FIG. 6, a flow diagram shows an illustrative method 40 according to one aspect of the present invention. The method begins at reference numeral 42. At reference numeral 44 the gas sensor is exposed to an environment containing a gas to be measured. At reference numeral 46, the temperature of the gas sensor is alternately controlled between a first temperature for a first period of time and a second temperature for a second period of time while the gas sensor is exposed to the gas. At reference numeral 48, an electrical characteristic of the gas sensor is continuously monitored during the first and second periods of time. This characteristic may be current, voltage, resistance, capacitance, or a characteristic of a semiconductor material. At reference numeral 50, the gas concentration is calculated as a function of a transient in the electrical characteristic of the sensor measured during the time that the temperature transitions between the first temperature and the second temperature. The method ends at reference numeral 52.

According to one embodiment of the present invention, the method may be performed continuously. Such a continuous performance of this method is shown by the feedback arrow from reference numeral 50 to reference numeral 44.

Figure 7:
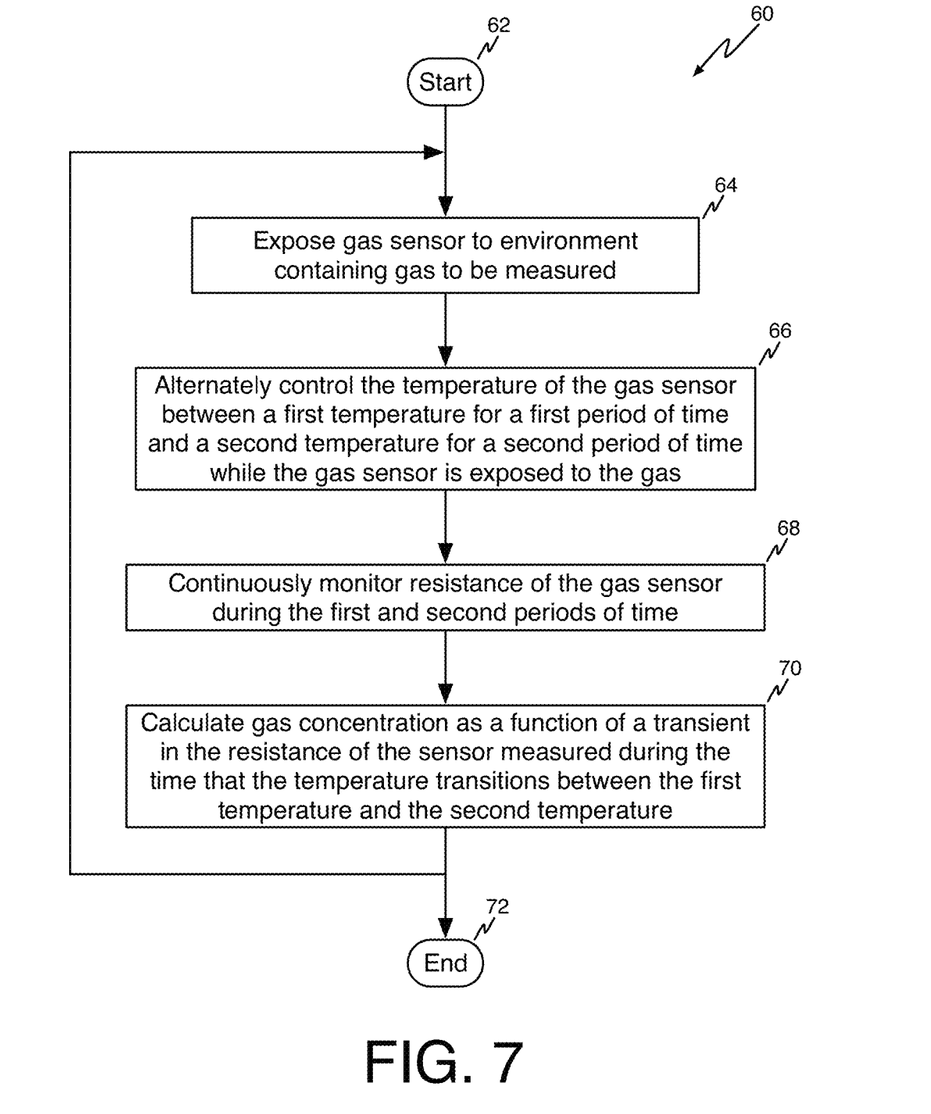
FIG. 7 is a flow diagram that shows an illustrative method according to another aspect of the present invention.

Referring now to FIG. 7, a flow diagram shows an illustrative method 60 according to another aspect of the present invention. The method begins at reference numeral 62. At reference numeral 64 the gas sensor is exposed to an environment containing a gas to be measured. At reference numeral 66, the temperature of the gas sensor is alternately controlled between a first temperature for a first period of time and a second temperature for a second period of time while the gas sensor is exposed to the gas. At reference numeral 68, an electrical characteristic of the gas sensor is continuously monitored during the first and second periods of time. This characteristic may be current, voltage, resistance, capacitance, or a characteristic of a semiconductor material. At reference numeral 70, the gas concentration is calculated as a function of a transient in the electrical characteristic of the sensor measured during the time that the temperature transitions between the first temperature and the second temperature. The method ends at reference numeral 72.

According to one embodiment of the present invention, the method may be performed continuously. Such a continuous performance of this method is shown by the feedback arrow from reference numeral 70 to reference numeral 64.

Figure 8:
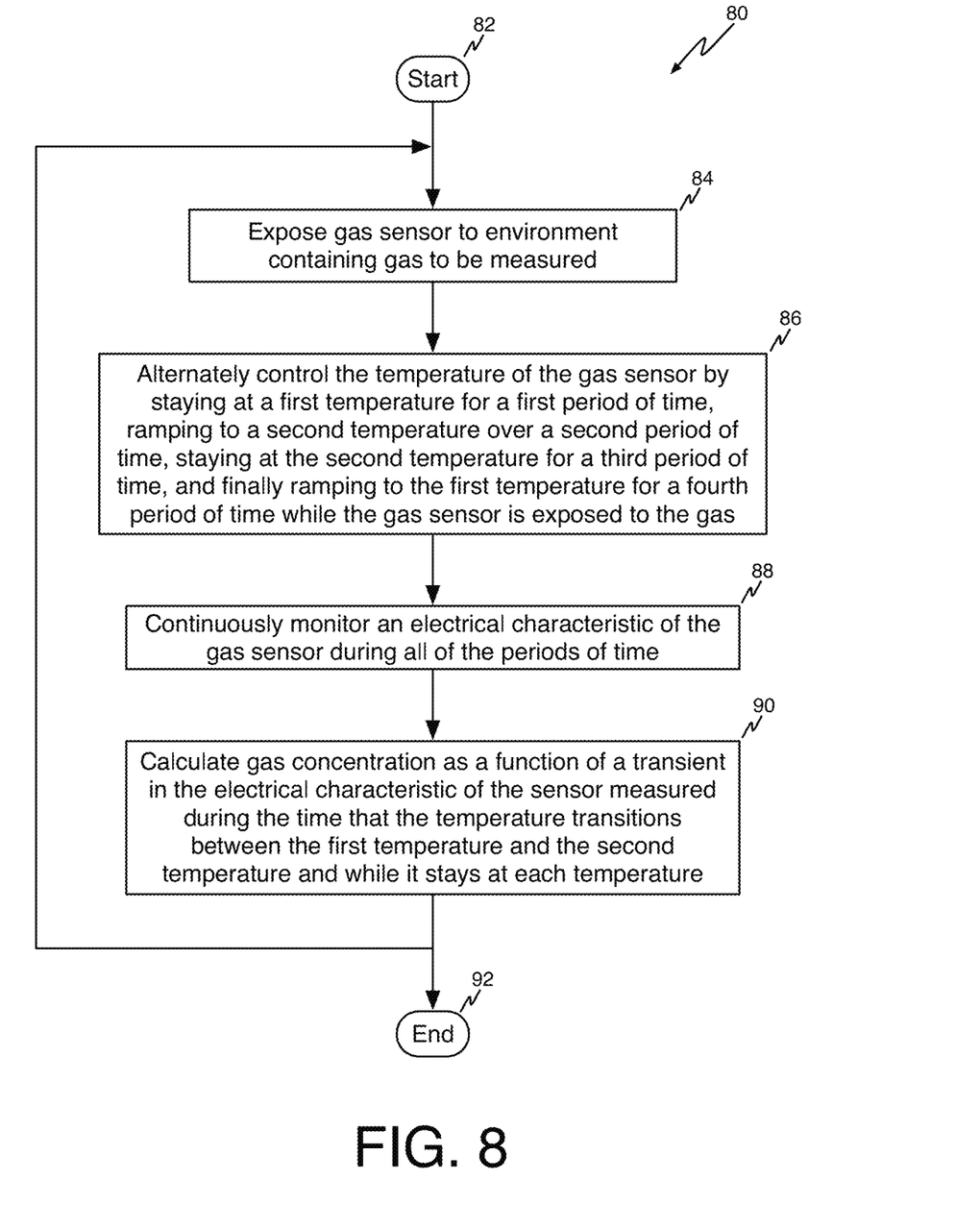
FIG. 8 is a flow diagram that shows an illustrative method according to another aspect of the present invention.

Referring now to FIG. 8, a flow diagram shows an illustrative method 80 according to another aspect of the present invention. The method begins at reference numeral 82. At reference numeral 84 the gas sensor is exposed to an environment containing a gas to be measured. At reference numeral 86, the temperature of the gas sensor is alternately controlled by staying at the first temperature for a first period of time, ramping to a second temperature over a second period of time, staying at the second temperature for a third period of time and finally ramping to the first temperature for a fourth period of time while the gas sensor is exposed to the gas. At reference numeral 88, an electrical characteristic of the gas sensor is continuously monitored during all the periods of time. This characteristic may be current, voltage, resistance, capacitance, or a characteristic of a semiconductor material. At reference numeral 90, the gas concentration is calculated as a function of a transient in the electrical characteristic of the sensor measured during the time that the temperature transitions between the first temperature and the second temperature. The method ends at reference numeral 92.

According to one embodiment of the present invention, the method may be performed continuously. Such a continuous performance of this method is shown by the feedback arrow from reference numeral 90 to reference numeral 84.

Figure 9:
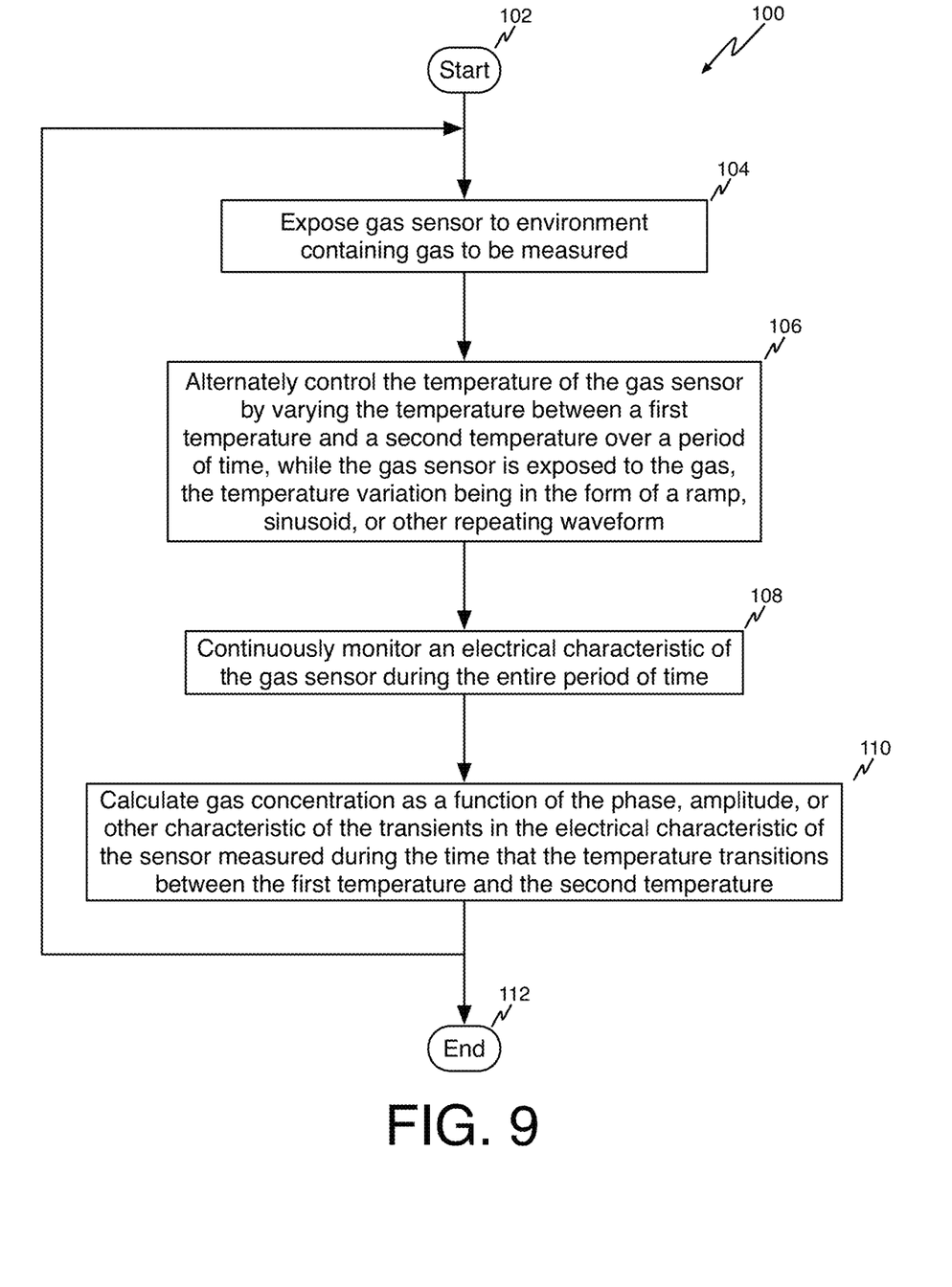
FIG. 9 is a flow diagram that shows an illustrative method according to another aspect of the present invention.

Referring now to FIG. 9, a flow diagram shows an illustrative method 100 according to another aspect of the present invention. The method begins at reference numeral 102. At reference numeral 104 the gas sensor is exposed to an environment containing a gas to be measured. At reference numeral 106, the temperature of the gas sensor is alternately controlled by continuously varying the temperature between a first temperature and a second temperature over a period of time while the gas sensor is exposed to the gas. This temperature variation can be in the form of a ramp, sinusoid, or other repeatable waveform. At reference numeral 108, an electrical characteristic of the gas sensor is continuously monitored during the entire period of time. This characteristic may be current, voltage, resistance, capacitance, or a characteristic of a semiconductor material. At reference numeral 110, the gas concentration is calculated as a function of transients in the electrical characteristics of the sensor measured during the time that the temperature transitions between the first temperature and the second temperature. The method ends at reference numeral 112.

According to one embodiment of the present invention, the method may be performed continuously. Such a continuous performance of this method is shown by the feedback arrow from reference numeral 110 to reference numeral 104.

The embodiments discussed previously describe a square wave temperature input. Other embodiments may include other types of thermal inputs, such as continuously varying triangle or sinusoidal patterns. A phase delay or another characteristic in the response of the sensor would then be one possible measurement of the H2 concentration around the sensor. Other measurement methods are also possible.

Although the present invention has been discussed in considerable detail with reference to certain preferred embodiments, other embodiments are possible. Therefore, the scope of the appended claims should not be limited to the description of preferred embodiments contained in this disclosure.

The present invention has been disclosed with reference to sensing H2 gas. Gas sensors may include materials that are sensitive to the presence of the specific gas being detected. Non-exhaustive examples of some materials that could be used for a hydrogen gas sensor include palladium, platinum, iridium, nickel, tungsten oxide, or alloys of palladium, platinum, iridium or nickel.

The gas sensors used in the method of the present invention may include resistor sensors, capacitor sensors, and semiconductor sensors such as transistor, or diode sensors. Capacitor, diode, and transistor gas sensors are known in the art. Examples include MOS capacitive sensors for H2 made from Pd and Pd alloys as shown in references 1, 2, and 3.

What is claimed is:

1. A method for measuring hydrogen concentration in a gas comprising:
    exposing a gas sensor to the gas, the gas sensor having an electrical characteristic that varies as a function of concentration of the gas;
    alternately controlling the temperature of the gas sensor between a first temperature and a second temperature while the gas sensor is exposed to the gas, wherein the temperature of the gas sensor remains at the first temperature over a first period of time, transitions from the first temperature to the second temperature over a second period of time, remains at the second temperature over a third period of time, and transitions from the second temperature to the first temperature over a fourth period of time, wherein in the presence of the hydrogen, the electrical characteristic of the gas sensor exhibits a spiking transient in response to the transition from the first temperature to the second temperature of the gas sensor, wherein the spiking transient returns to a steady state during the third period of time, wherein the spiking transient is an overshoot of the steady state;
    continuously monitoring the electrical characteristic of the gas sensor during the second period of time; and
    calculating the hydrogen concentration as a function of the spiking transient in the electrical characteristic of the gas sensor measured in response to the temperature transitioning from the first temperature to the second temperature.

2. The method of claim 1 wherein the electrical characteristic is resistance.

3. The method of claim 1 wherein the electrical characteristic is capacitance.

4. The method of claim 1 wherein exposing the gas sensor to the gas comprises exposing a thin-film gas sensor formed from an alloy of Pd to the gas.

5. The method of claim 4 wherein exposing the thin-film gas sensor formed from the alloy of Pd to the gas comprises exposing a PdNi thin-film gas sensor to the gas.

6. The method of claim 1 wherein exposing the gas sensor to the gas comprises exposing a PdAg thin-film gas sensor to the gas.

7. The method of claim 1, further comprising continuously monitoring the electrical characteristic of the gas sensor in response to the transition from the second temperature to the first temperature, and calculating the hydrogen concentration as a function of a second spiking transient in the electrical characteristics of the gas sensor measured in response to the temperature transitioning from the second temperature to the first temperature.

8. A method for measuring element concentration in a gas, comprising:
    exposing a gas sensor to the gas, the gas sensor having an electrical characteristic that varies as a function of concentration of the gas;
    alternately controlling the temperature of the gas sensor by staying at a first temperature for a first period of time, transitioning to a second temperature over a second period of time, staying at the second temperature for a third period of time, and then transitioning to the first temperature for a fourth period of time while the gas sensor is exposed to the gas;
    continuously monitoring the electrical characteristic of the gas sensor during the first, second, third and fourth periods of time, wherein the electrical characteristic exhibits a steady state at the second temperature, wherein in the presence of the hydrogen, the electrical characteristic of the gas sensor exhibits a spiking transient in response to transitions in the temperature of the gas sensor, wherein the spiking transient is an overshoot of the steady state; and
    calculating the gas concentration as a function of the spiking transient in the electrical characteristic of the gas sensor.

9. The method of claim 8 wherein the electrical characteristic is resistance.

10. The method of claim 8 wherein the electrical characteristic is capacitance.

11. The method of claim 8 wherein exposing the gas sensor to the gas comprises exposing a thin-film gas sensor formed from an alloy of Pd to the gas.

12. The method of claim 11 wherein exposing the thin-film gas sensor formed from an alloy of Pd to the gas comprises exposing a PdNi thin-film gas sensor to the gas.

13. The method of claim 8 wherein exposing the gas sensor to the gas comprises exposing a PdAg thin-film gas sensor to the gas.

14. The method of claim 8, wherein the gas concentration is calculated based on a slope of the spiking transient of the electrical characteristic as the spiking transient returns to the steady state.

15. The method of claim 14, further comprising:
calculating a drift in the gas sensor dynamically as the temperature of the gas sensor changes; and
accounting for the drift in calculating the hydrogen concentration.

16. The method of claim 15, wherein accounting for the drift comprises dynamically calculating a proportionality constant during the change in temperature.

17. A method for measuring hydrogen concentration in a gas, comprising:
exposing a gas sensor to the gas, the gas sensor having an electrical characteristic that varies as a function of concentration of the gas and a temperature of the gas sensor;
applying an electrical signal to control the temperature of the gas sensor over a period of time, while the gas sensor is exposed to the gas, the electrical signal being applied in the form of a repeating waveform;
continuously measuring the electrical characteristic of the gas sensor during the time of the repeating waveform; and
calculating the hydrogen concentration as a function of a spiking transient electrical characteristic of the sensor corresponding to the repeating waveform.

18. The method of claim 17 wherein the electrical characteristic is resistance.

19. The method of claim 17 wherein the electrical characteristic is capacitance.

20. The method of claim 17, wherein exposing the gas sensor to the gas comprises exposing a thin-film gas sensor formed from an alloy of Pd to the gas.

21. The method of claim 20 wherein exposing the thin-film gas sensor formed from an alloy of Pd to the gas comprises exposing a PdNi thin-film gas sensor to the gas.

22. The method of claim 17 wherein exposing the gas sensor to the gas comprises exposing a PdAg thin-film gas sensor to the gas.

23. The method of claim 17, wherein the function for calculating gas concentration is based on a characteristic of the waveform selected from the group consisting of a phase and an amplitude.

* * * * *

UNITED STATES PATENT AND TRADEMARK OFFICE
CERTIFICATE OF CORRECTION

Page 1 of 1

PATENT NO.         : 10,605,795 B2
APPLICATION NO.    : 14/624400
DATED              : March 31, 2020
INVENTOR(S)        : Vikas Lakhotia et al.

It is certified that error appears in the above-identified patent and that said Letters Patent is hereby corrected as shown below:

On the Title Page

Item (72), the listing of inventors should be changed from:
"Vikas Lakhotia, Valencia, CA (US); An T. Nguyen Le, Sevenson Ranch, CA (US); G. Jordan Maclay, Richland Center, WI (US)"

To:
-- Vikas Lakhotia, Overland Park, KS (US); Tim Howard, Canyon Country, CA (US); Dylan Thomas, Santa Clarita, CA (US) --

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*